United States Patent [19]

Mittleman et al.

[11] 4,048,996
[45] Sept. 20, 1977

[54] DUAL INJECTION SITE

[75] Inventors: Herbert Mittleman, Deerfield; Joseph L. Schopen, Crystal Lake, both of Ill.

[73] Assignee: Baxter Travenol Laboratories, Inc., Deerfield, Ill.

[21] Appl. No.: 695,703

[22] Filed: June 14, 1976

[51] Int. Cl.$^2$ .............................................. A61M 5/00
[52] U.S. Cl. .............................. 128/214 R; 128/214.2
[58] Field of Search ............. 128/214 R, 214 C, 214.2

[56] References Cited
U.S. PATENT DOCUMENTS

| | | | |
|---|---|---|---|
| 3,332,418 | 7/1967 | Brody | 128/214 R |
| 3,982,534 | 9/1976 | Buckman | 128/214 C |
| 3,990,445 | 11/1976 | Lundquist | 128/214 R |
| 4,000,740 | 1/1977 | Mittleman | 128/214 R |

Primary Examiner—Dalton L. Truluck
Attorney, Agent, or Firm—George H. Gerstman; Paul C. Flattery; John P. Kirby, Jr.

[57] ABSTRACT

A dual injection site for use in transmitting parenteral fluid is provided in the illustrative embodiment, by joining a pair of symmetrically shaped members each having a passage serving as either an inlet or an outlet for parenteral fluid flow. A pair of pierceable, self-sealing diaphragms are sandwiched between the members and each diaphragm is aligned with a respective passage.

23 Claims, 9 Drawing Figures

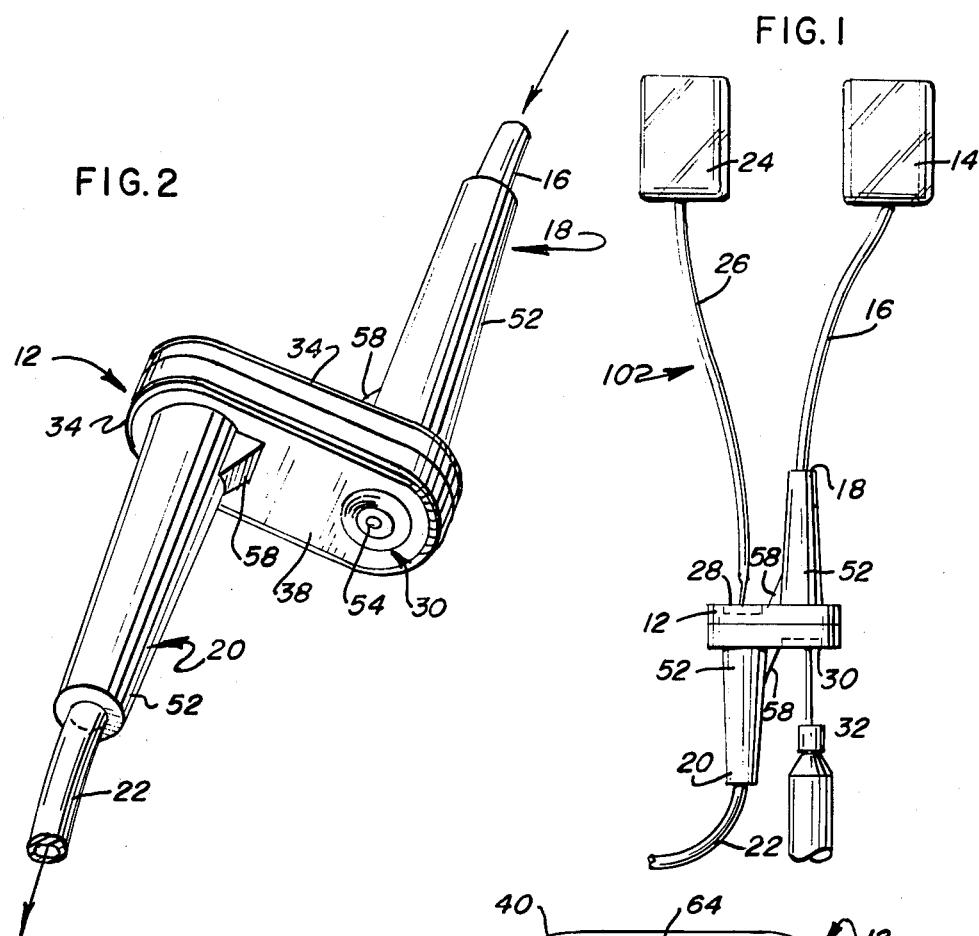
FIG. 1
FIG. 2
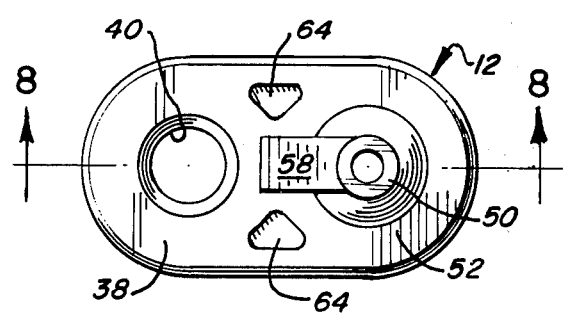
FIG. 3
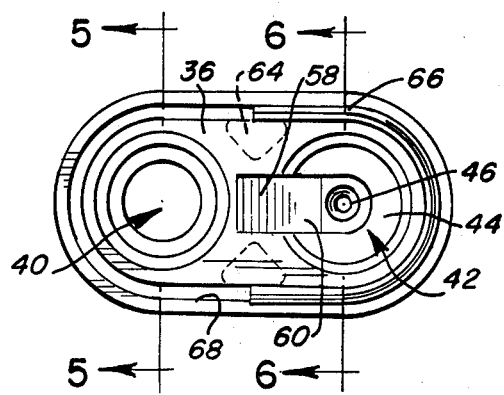
FIG. 4
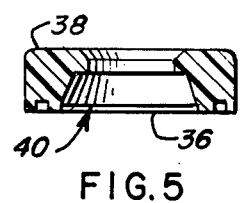
FIG. 5

DUAL INJECTION SITE

BACKGROUND OF THE INVENTION

This invention relates in general to an improved and more versatile injection site for use in transmitting a parenteral fluid.

Injection sites are commonly used in hospitals to provide a parenteral fluid delivery system in which supplementary parenteral fluid can be introduced into a conduit or passageway carrying a primary parenteral fluid to a patient without disturbing the delivery of the primary fluid or the patient. A parenteral fluid as used in this application includes a wide variety of fluids or medicaments utilized in medical treatment.

Thus the injection site receives the primary parenteral fluid via a first inlet connected through a flexible conduit usually to a reservoir and a second flexible conduit extends from the outlet of the injection site to an appropriate device for administering the fluid or liquid to a patient. The injection site also typically includes a second inlet sealed by a pierceable diaphragm. If it is necessary to introduce a supplementary fluid or medicament or blood to the patient, the fluid is injected through the diaphragm covering the second inlet, generally by means of a hypodermic syringe or a needle coupled to a container (i.e., "piggy back"), for combination with the primary parenteral fluid and administration to the patient.

If it may be necessary to inject several supplementary fluids, additional sites are generally provided by cutting the line at several positions thereby complicating the delivery system and introducing undesirable turbulence. Alternatively, several positions for injecting supplementary fluid may be provided on one side or top of an asymmetrically shaped site. However, these may be inconveniently located or too crowded for simultaneous use, as when a large syringe is used. Further, the asymmetric site shape and the problem of retaining the diaphragm results in a relatively large number of different parts and in complex and expensive molds and assembly procedures.

Accordingly, it is an object of the present invention to provide an injection site into which a plurality of supplementary parenteral fluids may be simultaneously conveniently introduced.

It is another object of the present invention to provide an injection site that can be facilely assembled in a system for administering parenteral fluid to a patient.

It is another object of the present invention to provide an injection site which can pass both a primary and a secondary parenteral fluid in either of two directions.

A further object of the present invention is to provide an injection site which enables a secondary fluid to be introduced into a primary fluid coaxially with the primary fluid to minimize flow disturbance.

An additional object of the present invention is to provide an injection site which accepts a needle and needle withdrawal without coring and leakage.

Another object of the present invention is to provide an injection site that is simple to manufacture and is relatively inexpensive to produce.

Other objects and advantages of the present invention will become apparent as the description proceeds.

BRIEF DESCRIPTION OF THE INVENTION

In accordance with the present invention, there is provided an injection site formed of two symmetrical or identical members to establish a chamber or passageway providing fluid communication between an inlet connected to a source of primary parenteral fluid and an outlet for delivering the parenteral fluid to a patient. Each member has a first port adapted to serve as either the inlet or as the outlet, and a second port or inlet is provided in each member adapted to receive a supplementary parenteral fluid.

Each second port is covered or closed by an identical self-sealing pierceable diaphragm captured between the members under compression laterally and transversely and is coaxially aligned with one of the first ports to enable two supplementary fluids to be conveniently simultaneously injected into the primary fluid with one supplementary fluid injected coaxially with the flow through the outlet port.

A more detailed explanation of the invention is provided in the following description and claims, and is illustrated in the accompanying drawings.

BRIEF DESCRIPTION OF THE DRAWINGS

FIG. 1 is a schematic view illustrating the relevant portion of a system for administering parenteral fluid to a patient and utilizing an injection site employing the principles of the present invention;

FIG. 2 is an isometric view of an injection site constructed in accordance with the principles of the present invention;

FIG. 3 is a top plan view of an injection site constructed in accordance with the principles of the present invention;

FIG. 4 is an elevational view of the interior surface of one member of the injection site shown in FIG. 3;

FIG. 5 is a cross-sectional view taken along the plane of the line 5—5 in FIG. 4;

DETAILED DESCRIPTION OF THE ILLUSTRATIVE EMBODIMENT

Figures 6, 6A:
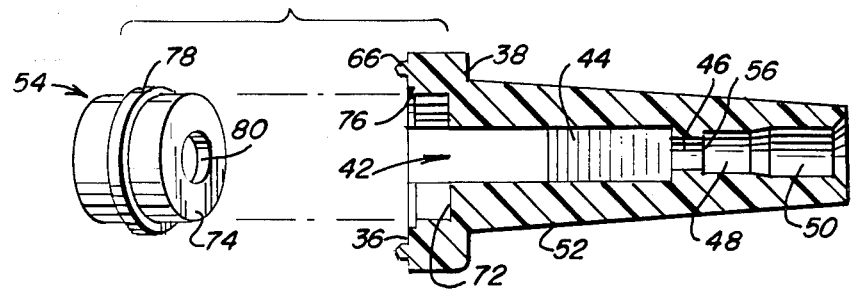
FIG. 6 is a cross-sectional view taken along the plane of the line 6—6 in FIG. 4.
FIG. 6A is an isometric view of a diaphragm for engagement with the portion of the site shown in FIG. 6.

Referring to FIG. 1, there is shown a system indicated generally by the reference character 10 for administering a parenteral fluid to a patient. The system 10 includes a dual injection site 12 for delivering a primary parenteral fluid from a source or container 14 through a flexible conduit 16 and through a serially connected port or inlet 18 and a port or outlet 20 in the injection site for delivery to a patient through a second flexible conduit 22. The injection site 12 may be taped to the patient or otherwise supported adjacent the position at which the fluid is administered to the patient, or it may be placed above the patient as during a surgical operation.

A source of secondary or supplemental parenteral fluid or blood is indicated by the reference character 24 and this secondary fluid is introduced into the primary fluid by means of a conduit 26, for example, connected at one end to the source 24 and having a hypodermic needle connected at the other end for piercing a self-sealing inlet 28 at the injection site 12. Another supplementary parenteral fluid may be simply introduced at a second self-sealing inlet 30 by means of a hypodermic syringe indicated at 32 for introducing additional secondary fluid. It will be understood that one of the major uses for the injection site 12 of the present invention is in anesthesiology administration sets or for IV fluids.

Figure 7:
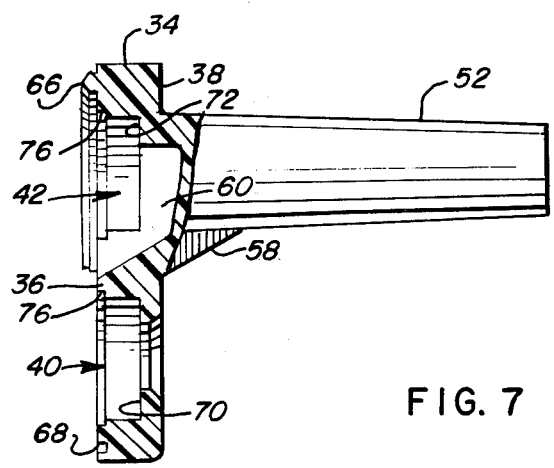
FIG. 7 is a side elevational view partially broken away of one member of an injection site constructed in accordance with principles of the present invention.
Figure 8:
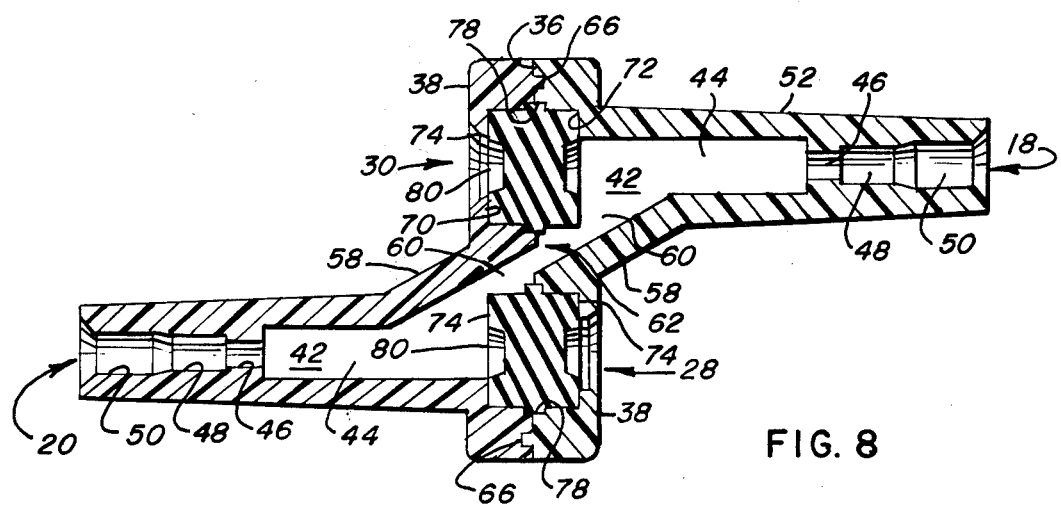
FIG. 8 is a cross-sectional view of an injection site taken along the plane of the line 8—8 in FIG. 3.

The site 12 includes a main body portion formed from two identical members or walls 34 of a plastic material, such as a polyolefin material, each having an internal surface 36 for mating engagement and an external surface 38 of generally flat or planar contour. Each member 34 is provided with a pair of laterally spaced passages 40 and 42 as best seen in FIGS. 3–8.

The passage 40 extends between the interior surface 36 and exterior surface 38 of the respective member 34 and passage 42 extends from the interior surface 36 through aligned ports or bores 44, 46, 48 and 50 formed in a projecting tube or annularly-shaped boss 52, which defines either inlet 18 or outlet 20. Boss 52 is integrally formed on the respective member 34 and extends perpendicularly from the external surface 38. The passage 40 in one wall 34 is aligned with a passage 42 in the other wall 34 of the site 12 and a self-sealing pierceable cylindrical insert, or diaphragm 54, of silicone rubber, latex or polyisoprene, for example, is seated in each of the aligned passages 40 and 42 to prevent fluid communication from bore 44 through the passage 40 and define the self-sealing ports or inlets 28 and 32.

A shoulder 56 is formed between bores 48 and 50 for seating one end of a conduit received in bores 48 and 50 and sealed in the bores generally by ultrasonic welding. A guideway portion is also formed for the conduit at the open end of bore 50.

Each boss 52 is also provided with an enlarged wall portion 58 radially extending toward one adjacent passage 40 to provide a widened section or portion 60 in bore 44 which extends through the respective wall 34 past the midpoint and is aligned with a similar widened portion 60 in the other wall or member 34 to form a chamber 62 for communicating fluid from the inlet 18 at a shallow or small angle to the outlet 20 and enabling communication of fluid from inlets 28 and 30, to outlet 20.

Member 34 is generally flat or planar with arcuate or generally circular end surfaces interconnected by straight parallel segments or surfaces and the external surface 38 is provided with a pair of spaced guide recesses 64 intermediate the passages 40 and 42, as best seen in FIG. 3, for aiding in the automatic assembly of the device and for providing uniform wall sections.

The interior surface 36 of each member 34 is provided with a bead or raised rim 66 generally following the peripheral contour of the member 34 and spaced inwardly therefrom. Each bead 66 extends substantially through one-half the distance around the wall and a recess 68 extends from one end of the bead 66 to the other end of the bead 66 with the recess 68 also following the contour of the wall so that each bead 66 and recess 68 encircle each of the passageways 40 and 42 in the respective wall 34. Each bead 66 is nestingly received in the recess 68 of the mating member 34 when the walls 34 are assembled to each other to automatically align the passageway 40 in each wall 34 with the passageway 42.

Each passage 40 and 42 is provided with a reduced diameter portion to form a respective shoulder 70 and 72 spaced from the interior surface 36 for seating against a respective end face 74 of the diaphragm 54, to retain and compress the diaphragm 54. An enlarged diameter groove portion 76 is formed in the interior surface 36 of each wall coaxial with each passage 40 and 42 for seating a peripheral bead 78 formed on each diaphragm 54 intermediate the end faces and bead 78 is retained under compression to ensure against leakage.

The external compression provided around the periphery of diaphragm 54 aids in preventing coring (removal of the portion being pierced) and also aids in preventing leaking.

Each diaphragm 54 is also provided with a recess 80 in each end face 74 to provide a relatively thinner section therebetween for facilitating piercing and preventing coring. The recesses 80 are aligned with a guideway portion for each passage 40 extending from the exterior surface 38 of each wall and aligned with the recess 80 to aid in guiding a syringe needle into the recess 80.

The site 12 is assembled simply and easily by placing a diaphragm in each of the passageways 40 and 42 of one symmetrical member 34 and then simply aligning the identically shaped mating member therewith so that the bead 66 on one member 34 is aligned with the recess 68 on the other member to also align the passageway 40 in one wall with the passage 42 in the other wall. The members 34 are thus engaged with the diaphragms 54 therebetween under compression in each direction and the two members 34 are secured together by sonic-welding, for example, to form a sealed secure joint therebetween. It will be noted that members 34 are formed from identical relatively inexpensive molds, as are diaphragms 54.

In use as shown, for example, by the system 10 in FIG. 1, either of the bosses 52 is arranged to receive either of the conduits 16 or 22, which is then secured in the selected boss. The boss 52 receiving conduit 16 serves as inlet 18 and fluid communication proceeds from the container 14 through the conduit 16, one bore 46, chamber 62 and the other bore 46 and through the conduit 22 in the boss serving as outlet 20 for delivery to the patient.

One secondary or supplementary parenteral fluid is introduced from reservoir 24, for example, by the hypodermic needle 28 at the end of conduit 26 piercing through self-sealing diaphragm 54 in inlet 28 coaxial with the outlet 20. The other parenteral or secondary fluid is introduced through the other diaphragm in the inlet 30 by means of the hypodermic syringe needle 32. It will be noted that the site 12 may be connected for flow in either direction therethrough and still allow secondary fluid to be easily injected and that the elongated bosses enable a long length of needle to be inserted, while the location and size of the inlets 28 and 30 enables the convenient use of large needles for introducing sufficient quantities of supplementary fluid without regard to the site orientation.

It is to be understood that various modifications and substitutions may be made by those skilled in the art without departing from the novel spirit and scope of the invention.

What is claimed is:

1. An injection site for location between a parenteral source of fluid and a patient, which comprises: a first inlet for coupling to a conduit from a first liquid container; a second inlet having a pierceable, self-sealing diaphragm positioned therein; a third inlet having a pierceable, self-sealing diaphragm positioned therein; an outlet for coupling to a conduit for connection to a patient; and a main body portion having a chamber coupling said first, second and third inlets to said outlet, said first inlet and said outlet being oppositely positioned and said second and third inlets being oppositely positioned, said second inlet and said outlet being substantially coaxial, and said third inlet being substantially coaxial with said first inlet.

2. An injection site as described in claim 1, wherein the diaphragm in said second and third inlets is held under compression.

3. An injection site as described in claim 1, wherein said first inlet and said outlet are laterally displaced from each other.

4. An injection site as described in claim 1, wherein said first inlet and said outlet are parallely positioned.

5. An injection site as described in claim 1, wherein said body portion comprises two symmetrical members each having a first passage adapted to serve as either said first inlet or as said outlet.

6. An injection site as described in claim 5, in which each passage is laterally displaced from the other passage.

7. An injection site as described in claim 5, in which each member includes a second passage laterally displaced from the first passage for coaxial communication with the first passage in the other member.

8. An injection site as described in claim 5, in which said diaphragm is held between said members under compression.

9. An injection site as described in claim 8, in which the diaphragm has a bead held under compression.

10. An injection site as described in claim 5, wherein a bead and recess on each member engage in encircling relationship to each of said passages.

11. An injection site as described in claim 5, in which one member has a bead and the other member has a recess engaged with said bead and secured thereto.

12. An injection site as described in claim 5, wherein each member includes a tubular boss through which said first passage extends.

13. An injection site as described in claim 12, wherein each member includes a wall extending perpendicular to said boss and having a second passage therein.

14. An injection site for enabling the introduction of a supplementary parenteral fluid into a primary parenteral fluid being transmitted from a source to a patient, the improvement comprising: a body having first and second ports for use either as an inlet or a outlet for passing said primary parenteral fluid through said body from said first port to said second port or for passing said primary parenteral fluid through said body from said second port to said first port, and pierceable diaphragm means enabling said supplementary fluid to be injection into said primary fluid at a position in said body intermediate said ports, said pierceable diaphragm means including a first diaphragm coaxially positioned with respect to said first port and a second diaphragm coaxially positioned with respect to said second port.

15. The site claimed in claim 14, in which said pierceable diaphragm means enables the simultaneous injection of two supplementary fluids.

16. The injection site claimed in claim 14, in which said body is formed by two symmetrical members, with each member including one of said ports and one of said diaphragms.

17. The injection site claimed in claim 16, in which each symmetrical member includes a wall having a tubular boss thereon forming one port, and said means comprises a second passage in each wall adapted to be aligned with the port in the boss formed on the other wall.

18. The injection site claimed in claim 17, in which each wall includes sealingly bonded means encircling each passage and diaphragm.

19. An injection site for location between a parenteral source of fluid and a patient, which comprises: a main body portion; a first inlet on one side of said body portion for coupling to a conduit from a first liquid container; a second inlet on said one side of said body portion, laterally displaced from said first inlet, and having a pierceable, self-sealing diaphragm positioned therein and held under compression; an outlet on the opposite side of said body portion and laterally displaced from said inlet for coupling to a conduit connected to a patient, a third inlet on said opposite side of said body portion and laterally displaced from said outlet, said third inlet having a pierceable, self-sealing diaphragm positioned therein and held under compression; said main body portion having a chamber coupling said first, second and third inlets and said outlet, said second inlet being positioned for injection from said first side and said third inlet being positioned for injection from said opposite side.

20. An injection site as described in claim 19, wherein said second inlet and said outlet are substantially coaxial, and said third inlet is substantially coaxial with said first inlet.

21. An injection site as described in claim 19, wherein said body portion comprises two symmetrical member each having a first passage adapted to serve as either said first inlet or as said outlet.

22. An injection site for location between a parenteral source of fluid and a patient, which comprises: a main body portion, said main body portion comprising a first member and a second member, said first member having a first inlet and means laterally displaced from said first inlet receiving a pierceable diaphragm, said second member having an outlet and means laterally displaced from said outlet receiving a pierceable diaphragm, said first and second members being interconnectable with each other, said first and second members each carrying on its connecting side a bead extending substantially through one-half the distance around said side and a recess extending from one end of the bead to the other end of the bead, with said recess being symmetrical with said bead, whereby said first member and said second member can be interconnected with each other with the bead from the first member engaging the recess of the second member and the bead of the second member engaging the recess of the first member.

23. An injection site as described in claim 22, in which said bead and recess encircle the fluid passageways defined by each member.

* * * * *